United States Patent
Greenspan et al.

(10) Patent No.: US 11,841,281 B2
(45) Date of Patent: Dec. 12, 2023

(54) FLEXIBLE PRESSURE SENSORS

(71) Applicant: Accenture Global Solutions Limited, Dublin (IE)

(72) Inventors: Mark Benjamin Greenspan, San Francisco, CA (US); Lavinia Andreea Danielescu, San Francisco, CA (US)

(73) Assignee: Accenture Global Solutions Limited, Dublin (IE)

( * ) Notice: Subject to any disclaimer, the term of this patent is extended or adjusted under 35 U.S.C. 154(b) by 329 days.

(21) Appl. No.: 17/338,225

(22) Filed: Jun. 3, 2021

(65) Prior Publication Data

US 2022/0390298 A1 Dec. 8, 2022

(51) Int. Cl.
*G01L 1/20* (2006.01)
*A41D 19/00* (2006.01)
*A61B 5/00* (2006.01)
*A43B 3/36* (2022.01)

(52) U.S. Cl.
CPC .......... *G01L 1/205* (2013.01); *A41D 19/0027* (2013.01); *A43B 3/36* (2022.01); *A61B 5/6806* (2013.01); *A61B 5/6807* (2013.01); *A61B 2562/0247* (2013.01)

(58) Field of Classification Search
CPC ....... G01L 1/205; A43B 3/36; A41D 19/0027; A61B 5/6806; A61B 5/6807; A61B 2562/0247
USPC .......................................................... 73/774
See application file for complete search history.

(56) References Cited

U.S. PATENT DOCUMENTS

| | | | |
|---|---|---|---|
| 2015/0153374 A1* | 6/2015 | Balakrishnan | G04G 21/00 |
| | | | 702/178 |
| 2017/0146413 A1* | 5/2017 | Ibrocevic | B25J 19/06 |
| 2017/0212769 A1* | 7/2017 | Yang | G06F 1/163 |
| 2018/0028862 A1* | 2/2018 | Statham | G09B 19/0038 |
| 2018/0202874 A1* | 7/2018 | Ibrocevic | G01L 1/14 |
| 2018/0202875 A1* | 7/2018 | Ibrocevic | G01L 1/2287 |
| 2019/0257015 A1* | 8/2019 | Harnett | H05K 1/00 |

OTHER PUBLICATIONS

3M, "Product Data Sheet: 3M™ Conductive Film Products," dated 2014, 3 pages.

(Continued)

*Primary Examiner* — Max H Noori
(74) *Attorney, Agent, or Firm* — Fish & Richardson P.C.

(57) ABSTRACT

Implementations are directed to a pressure-sensing device including a pressure-sensitive sheet, one or more pressure-sensitive input regions disposed along the pressure-sensitive sheet including a first conductive thread including a first length in contact with the pressure-sensitive sheet, and a second conductive thread including a second length in contact with the pressure-sensitive sheet. At least a first portion of the first length of the first conductive thread passes through the pressure-sensitive sheet through a first hole in the pressure-sensitive sheet at a first location and a second portion of the second length of the second conductive thread passes through the pressure-sensitive sheet through a second hole in the pressure-sensitive sheet at a second location.

16 Claims, 9 Drawing Sheets

(56) References Cited

OTHER PUBLICATIONS

Adafruit.com [online], "Firewalker LED Sneakers: Make Velostat Step Sensors," available on or before Sep. 2, 2013, via Internet Archive: Wayback Machine URL<https://web.archive.org/web/20130902032148/https://learn.adafruit.com/firewalker-led-sneakers/make-velostat-step-sensors>, retrieved on Jan. 3, 2022, retrieved from URL<https://learn.adafruit.com/firewalker-led-sneakers/make-velostat-step-sensors>; 16 pages.

Adafruit.com [online], "Firewalker LED Sneakers: Overview," available on or before Sep. 2, 2013, via Internet Archive: Wayback Machine URL<https://web.archive.org/web/20130902014917/https://learn.adafruit.com/firewalker-led-sneakers>, retrieved on Jan. 3, 2022, retrieved from URL<https://learn.adafruit.com/firewalker-led-sneakers>, 18 pages.

Adafruit.com [online], "Pressure-Sensitive Conductive Sheet (Velostat/Linqstat)," available on or before Jul. 7, 2013, via Internet Archive: Wayback Machine URL<https://web.archive.org/web/20130707074043/https://www.adafruit.com/product/1361>, retrieved on Jan. 3, 2022, retrieved from URL<https://www.adafruit.com/product/1361>; 7 pages.

GetCarv.com [online], "CARV: How it Works," available on or before Oct. 22, 2020, via Internet Archive: Wayback Machine URL<https://web.archive.org/web/20201022004905/https://getcarv.com/how-it-works>, retrieved on Jan. 3, 2022, retrieved from URL<https://getcarv.com/how-it-works>, 16 pages.

Kobakant.at [online], "Conductive Materials: Velostat," available on or before Jun. 5, 2011, via Internet Archive: Wayback Machine URL<https://web.archive.org/web/20110605153425/https://www.kobakant.at/DIY/?p=381>, retrieved on Jan. 3, 2022, retrieved from URL<https://www.kobakant.at/DIY/?p=381>, 7 pages.

Arion.run [online], "ARION wearable," available on or before Aug. 5, 2020 via Internet Archive: Wayback Machine URL<https://web.archive.org/web/20200805223715/https://www.arion.run/wearable/>, retrieved on Oct. 8, 2021, retrieved from URL<https://www.arion.run/wearable/>, 11 pages.

Dinesh et al., "Applications of E-textile Pressure Sensors," New Jersey's Governor's School of Engineering and Technology, Jul. 21, 2017, 9 pages.

GerCarv.com [online]. "CARV," available on or before Jan. 21, 2018 via Internet Archive: Wayback Machine URL<https://web.archive.org/web/20180121150246/https://getcarv.com/>; retrieved on Oct. 8, 2021, retrieved from URL<https://getcarv.com/>, 12 pages.

SensoriaFitness.com [online], "Sensoria Artificial Intelligence Sportswear," available on or before Jun. 27, 2013 via Internet Archive: Wayback Machine URL<https://web.archive.org/web/20130627164235/https://www.sensoriafitness.com/>, retrieved on Oct. 8, 2021, retrieved from URL<https://www.sensoriafitness.com/>; 10 pages.

Suprapto et al., "Low-Cost Pressure Sensor Matrix Using Velostat," Presented at Proceedings of the 5th International Conference on Instrumentation, Communications, Information Technology, and Biomedical Engineering (ICICI-BME), Bandung, Indonesia, Nov. 6-7, 2017, 137-140.

Tekscan.com [online], "F-Scan System," available on or before Feb. 2, 2016 via Internet Archive: Wayback Machine URL<https://web.archive.org/web/20160202032836/https://www.tekscan.com/products-solutions/systems/f-scan-system>, retrieved on Oct. 8, 2021, retrieved from URL<https://www.tekscan.com/products-solutions/systems/f-scan-system>, 5 pages.

\* cited by examiner

FLEXIBLE PRESSURE SENSORS

BACKGROUND

Force sensitive resistors (FSR) are a category of resistors whose resistive value can be altered depending on an applied force. FSRs can be utilized to detect applied physical pressure, compression, and weight.

SUMMARY

Implementations of the present disclosure are generally directed to a flexible pressure sensor. More particularly, implementations of the present disclosure are directed to a flexible pressure sensor device including a pressure-sensitive sheet and conductive thread stitched through portions of the pressure-sensitive sheet. The flexible pressure sensor can be utilized as a wearable device, e.g., in a shoe, to provide real-time force distribution feedback to a user.

In some implementations, the present disclosure provides a pressure-sensing device including a pressure-sensitive sheet, one or more pressure-sensitive input regions disposed along the pressure-sensitive sheet, each pressure-sensitive input region including a first conductive thread including a first length in contact with the pressure-sensitive sheet, and a second conductive thread including a second length in contact with the pressure-sensitive sheet. At least a first portion of the first length of the first conductive thread passes through the pressure-sensitive sheet through a first hole in the pressure-sensitive sheet at a first location and a second portion of the second length of the second conductive thread passes through the pressure-sensitive sheet through a second hole in the pressure-sensitive sheet at a second location.

Other implementations of this aspect include corresponding systems, apparatus, and computer programs, configured to perform the actions of the methods, encoded on computer storage devices.

These and other implementations can each optionally include one or more of the following features. In some implementations, the first conductive thread includes a first lead electrically connected to a positive electrode of the pressure-sensing device and the second conductive thread includes a second lead electrically connected to a negative electrode of the pressure-sensing device.

In some implementations, the pressure-sensitive sheet includes an electrically conductive material, where an electrical conductance of the pressure-sensitive sheet depends in part on an externally applied force to i) the pressure-sensitive sheet, ii) the first conductive thread, iii) the second conductive thread, or iv) a combination thereof. The pressure-sensitive sheet can include Velostat™.

In some implementations, the first length of the first conductive thread passes through the pressure-sensitive sheet through multiple holes in the pressure-sensitive sheet at a first set of multiple locations, and where the second length of the second conductive thread passes through the pressure-sensitive sheet through multiple holes at a second set of multiple locations. The first length of the first conductive thread can be substantially parallel to the second length of the second conductive thread. The first length of the first conductive thread and the second length of the second conductive can form a serpentine pattern.

In some implementations, the first conductive thread includes two or more lengths that are in contact with the pressure-sensitive sheet and substantially parallel to each other and substantially parallel to the second length of the second conductive thread.

In some implementations, the first length of the first conductive thread is in contact with a first surface of the pressure-sensitive sheet, and a third length of the first conductive thread is in contact with a second surface of the pressure-sensitive sheet opposite the first surface of the pressure-sensitive sheet.

The present disclosure further provides a system, including a pressure-sensing device including a pressure-sensitive sheet, and one or more pressure-sensitive input regions disposed along the pressure-sensitive sheet, each pressure-sensitive input region including a first conductive thread including a first length in contact with the pressure-sensitive sheet, and a second conductive thread including a second length in contact with the pressure-sensitive sheet. At least a first portion of the first length of the first conductive thread passes through the pressure-sensitive sheet through a first hole in the pressure-sensitive sheet at a first location and a second portion of the second length of the second conductive thread passes through the pressure-sensitive sheet through a second hole in the pressure-sensitive sheet at a second location. The system further includes one or more processors, and a computer-readable storage device coupled to the one or more processors and having instructions stored thereon which, when executed by the one or more processors, cause the one or more processors to perform operations including: detecting, from the pressure-sensing device, a change in electrical properties of the pressure-sensing device, and determining, from the detected change in electrical properties, a force applied to the pressure-sensing device.

These and other implementations can each optionally include one or more of the following features. In some implementations the system further includes a light source in data communication with the one or more processors, and a power source configured to provide power to the light source, where the light source is configured to emit light signal in response to the detected change in electrical properties.

In some implementations, the system further includes a shoe, where the pressure-sensing device is retained within a portion of the shoe. The system can further include generating, in response to the determined force applied to the pressure-sensing device, a stride adjustment recommendation, and providing, the stride adjustment recommendation. The light source can be retained within a portion of the shoe, and where providing the stride adjustment recommendation comprises emitting the light signal from the light source. Providing the stride adjustment recommendation can include providing a notification in a user interface on a user device. At least a portion of the pressure sensing device can be located between two seams of the shoe.

In some implementations, the system further includes a pressure-sensitive glove, where the pressure-sensing device is retained within a fingertip or palm of the pressure-sensitive glove.

In some implementations, the system includes generating, in response to the determined force applied to the pressure-sensing device, a force notification; and providing, the force notification.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

These and other embodiments can be incorporated to realize the following advantages. A flexible pressure sensor can be incorporated as a wearable device, e.g., in the sole and/or seams of a shoe, to provide low-cost, real-time feedback to a user, e.g., stride adjustment, material wear, localized bend/deformation of the wearable device, manufacturing quality control, etc. By directly incorporating conductive threads into the pressure-sensitive layer, e.g., a Velostat™ layer, the flexible pressure sensor can have a minimal profile and can have increased flexibility of the device. The thinner profile enables the pressure sensor to be used in applications in which other types of pressure sensors would not be practical, including use in wearables designed for comfort or performance. A sensor with the conductive threads through the pressure-sensitive layer can enable for the pressure sensor to be utilized for measuring forces applied parallel to a pressure-sensitive layer of the pressure sensor, and can allow for measuring of forces applied to the conductive thread that is embedded in the pressure-sensitive layer (e.g., where the conductive thread is embedded in a seam of a garment or shoe).

The details of one or more implementations of the present disclosure are set forth in the accompanying drawings and the description below. Other features and advantages of the present disclosure will be apparent from the description and drawings, and from the claims.

DETAILED DESCRIPTION

Implementations of the present disclosure are generally directed to a flexible pressure sensor. More particularly, implementations of the present disclosure are directed to a flexible pressure sensor device including a pressure-sensitive sheet and conductive thread stitched or otherwise routed through portions of the pressure-sensitive sheet. The flexible pressure sensor can be utilized as part of a wearable device, e.g., in a shoe or glove to provide real-time force distribution feedback to a user.

Figure 1A:
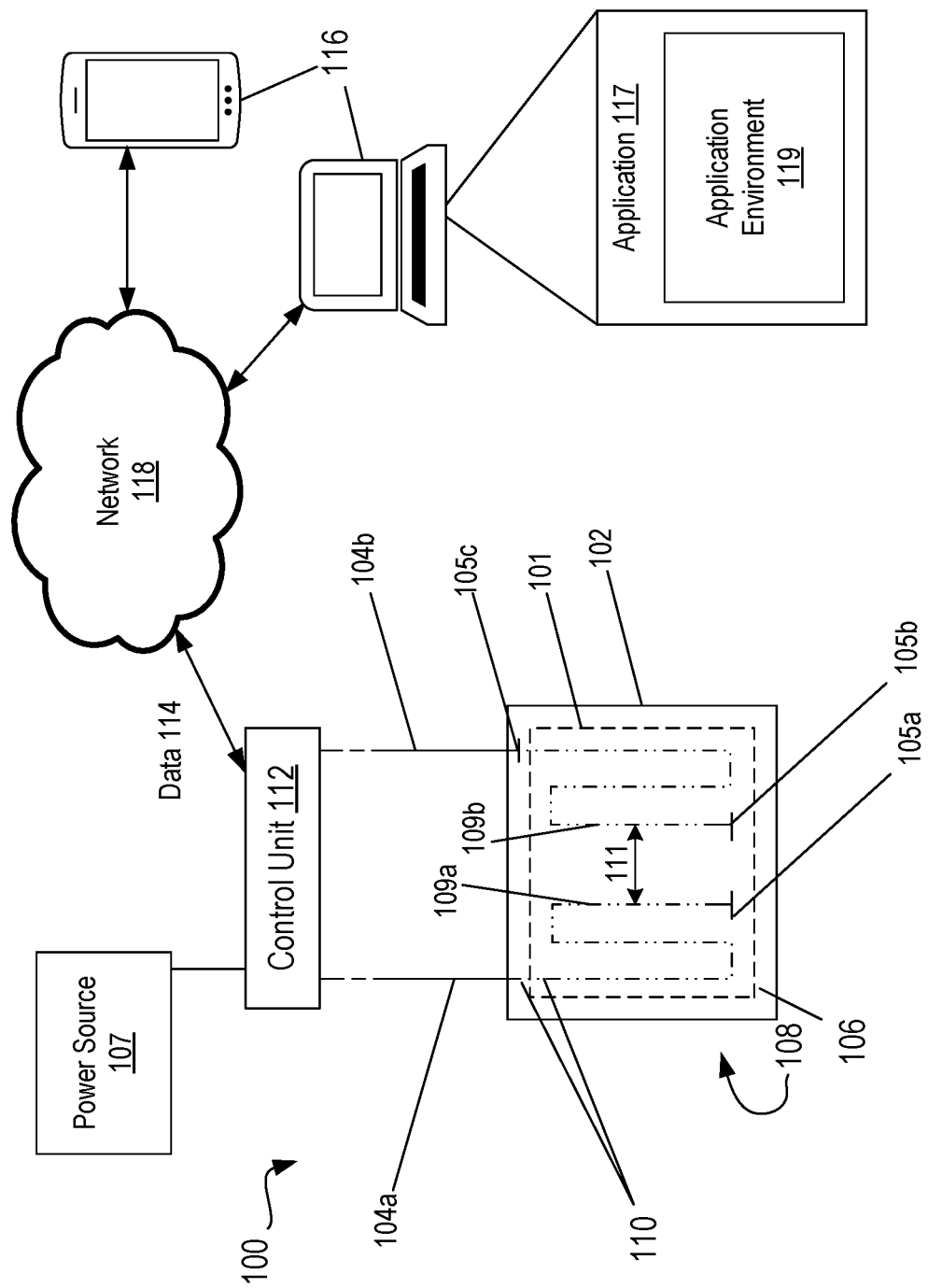
FIGS. 1A-1B depict schematic views of an example flexible pressure sensor.

FIG. 1A depicts a schematic of an example flexible pressure sensor. The flexible pressure sensor 100 includes a pressure-sensitive sheet 102, and a pressure-sensitive region 101 including a first electrode 104a, and a second electrode 104b. Pressure-sensitive sheet 102 can include one or more layers of a pressure-sensitive electrically conductive material (e.g., a piezoresistive material), where applied force (e.g., applied pressure, deformation, or flexing of the layer) can cause a change in the conductance of the material in the bulk of the layer. In other words, when a force is applied to the flexible pressure sensor, a resistance of the material can be reduced over a particular distance, e.g., due to a change in distance between carbon particles embedded in the material (e.g., embedded in the polyolefin).

In one example, the pressure-sensitive sheet 102 is a polymeric foil (e.g., polyolefins) impregnated with or embedded with carbon black such that the polymeric foil is electrically conductive, e.g., Velostat™ which is also referred to as Lingstat. The resistance of the pressure-sensitive sheet changes, e.g., decreases, when pressed. For example, the resistance of the pressure-sensitive conductive sheet can decrease with an increase in the amount of pressure applied to the pressure-sensitive conductive sheet.

First electrode 104a and second electrode 104b include a conductive thread, where the conductive thread includes a conductive material, e.g. a metallic or metalized fibers. In one example, conductive thread includes natural and/or synthetic fibers coated in a conductive metallic coating, e.g., silver-coated nylon thread. In another example, conductive thread is a conductive metal wire, e.g., stainless steel wire, copper wire, carbon nanotube or graphene yarns, or the like.

Figure 1B:
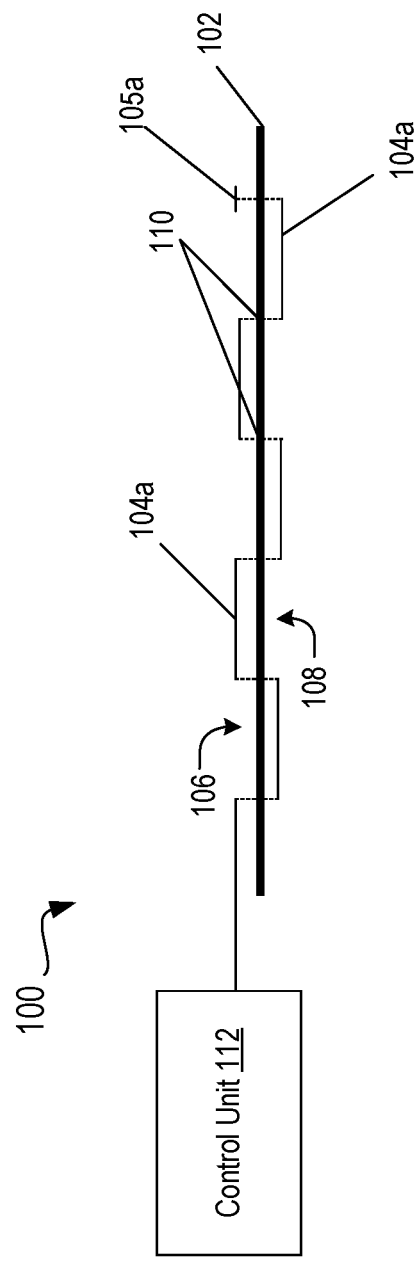

As depicted in a cross-sectional view of sensor 100 in FIG. 1B, the first electrode 104a and second electrode 104b are each stitched into the pressure-sensitive sheet 102 such that a portion of the electrodes 104a and/or 104b are in contact with the pressure-sensitive sheet 102 with a respective front surface 106 and back surface 108 of the pressure-sensitive sheet 102. The conductive thread of the electrodes 104a and 104b pass through the pressure-sensitive sheet 102 through multiple holes 110 at multiple locations of the pressure-sensitive sheet 102, e.g., using a running stitch or another sewing stitch.

In some implementations, multiple pressure-sensitive regions 101 can be defined on a pressure-sensitive sheet 102. Each pressure-sensitive region 101 can include a respective pair of electrodes. For example, the multiple pressure-sensitive regions 101 can be adjacent to each other on the pressure-sensitive sheet 102. In some implementations, the multiple pressure-sensitive regions 101 can be distributed on a pressure-sensitive sheet at locations of interest. For example, a pressure-sensitive sheet 102 can correspond to the area of a sole of a shoe, where the pressure-sensitive regions are located at the ball and heel locations of the sole of the shoe. In another example, the pressure-sensitive regions can be distributed throughout the sole of the shoe, along sides of the shoe (e.g., where the side of the shoe meets the sole, and/or other locations within a shoe. Further details of one example implementation are described below with reference to FIG. 2A.

In some implementations, the first electrode 104a and/or second electrode 104b can be affixed to the pressure-sensitive sheet 102 at a respective point 105a and point 105b, e.g., using a stitch, fastener, adhesive, solder, or the like. For example, the first electrode 104a can be affixed to the pressure-sensitive sheet 102 at an end point of the first electrode. In some implementations, the first electrode 104a and/or second electrode 104b can be affixed to the pressure-sensitive sheet 102 at multiple points, for example, where the second electrode 104b is affixed at 105a and 105c.

Though the first electrode 104a and second electrode 104b are depicted in FIG. 1A and FIG. 1B as sewn in a particular pattern on the pressure-sensitive sheet 102, other patterns are possible, as described below with reference to FIG. 2B. In some implementations, the first electrode 104a and second electrode 104b are sewn into the pressure-sensitive sheet 102 such that a length 109a of the first electrode 104a and a length 109b of the second electrode 104b are arranged substantially parallel to each other and separated by a gap 111. The size of the gap 111 can vary in different implementations based on the desired accuracy of the pressure detection.

Referring back to FIG. 1A, the flexible pressure sensor 100 can be in data communication with, e.g., electrically connected to, a control unit 112. The control unit 112 can include a microcontroller, for example, an Arduino microcontroller, which may be enabled with wireless communication capabilities, e.g., Bluetooth, Wi-Fi, etc., and a power source 107, e.g., a lithium ion battery, configured to provide power to the control unit 112, flexible pressure sensor, etc. In some implementations, power source 107 can include energy harvested from a piezoelectric sensor (e.g., that charges with movement/pressure of the wearable device). The control unit 112 can perform electrical measurements to determine resistance changes in the flexible pressure sensor 100 in real-time. In some implementations, the flexible pressure sensor can be calibrated, such that a relationship between an amount of applied force can be correlated to an electrical measurement between the first and second leads 104a,b of the sensor 100.

Electrical measurements between the electrodes 104a, 104b can be performed by a control unit 112 in electrical contact with the electrodes 104, 104b. For example, resistance measurements can be performed between the first electrode 104a (e.g., positive electrode) and second electrode 104b (e.g., return electrode). In one example, the resistance of the pressure-sensitive conductive sheet between the positive and return (negative) electrode(s) decreases, resulting in a change in voltage (e.g. a increase in voltage) that can be detected on the return electrode. This change in voltage can be measured by a microcontroller. In some implementations, a pull-down resistor can be incorporated between the return electrode and the microcontroller to increase the accuracy of the change in voltage detected by the microcontroller.

In some implementations, data 114 collected by the control unit 112, e.g., electrical resistance data, can be provided to user devices 116 over a network 118. User devices can include, for example, smart phone, computer, cloud-based servers, or the like. User device 116 can include an application 117 for processing data 114 collected by the control unit 112 and presenting the processed data 114 in an application environment 119 to a user. In one example, users could be notified while running if pronating or supinating, which could lead to injury. In another example, the system can notify the user if they bend their elbow too far or not enough for an optimal basketball shot, or if the user's elbow is too far from their body.

In some implementations, notification can be provided, for example, in the form of real-time conversational feedback through a companion app on a phone, in the form of post run visual feedback in a companion app on the phone, or in the form of haptic feedback on the body or within the shoe itself (e.g., putting too much pressure on the inside of the sole can cause the inside of the sole to vibrate until the pressure is corrected).

Figure 1C:
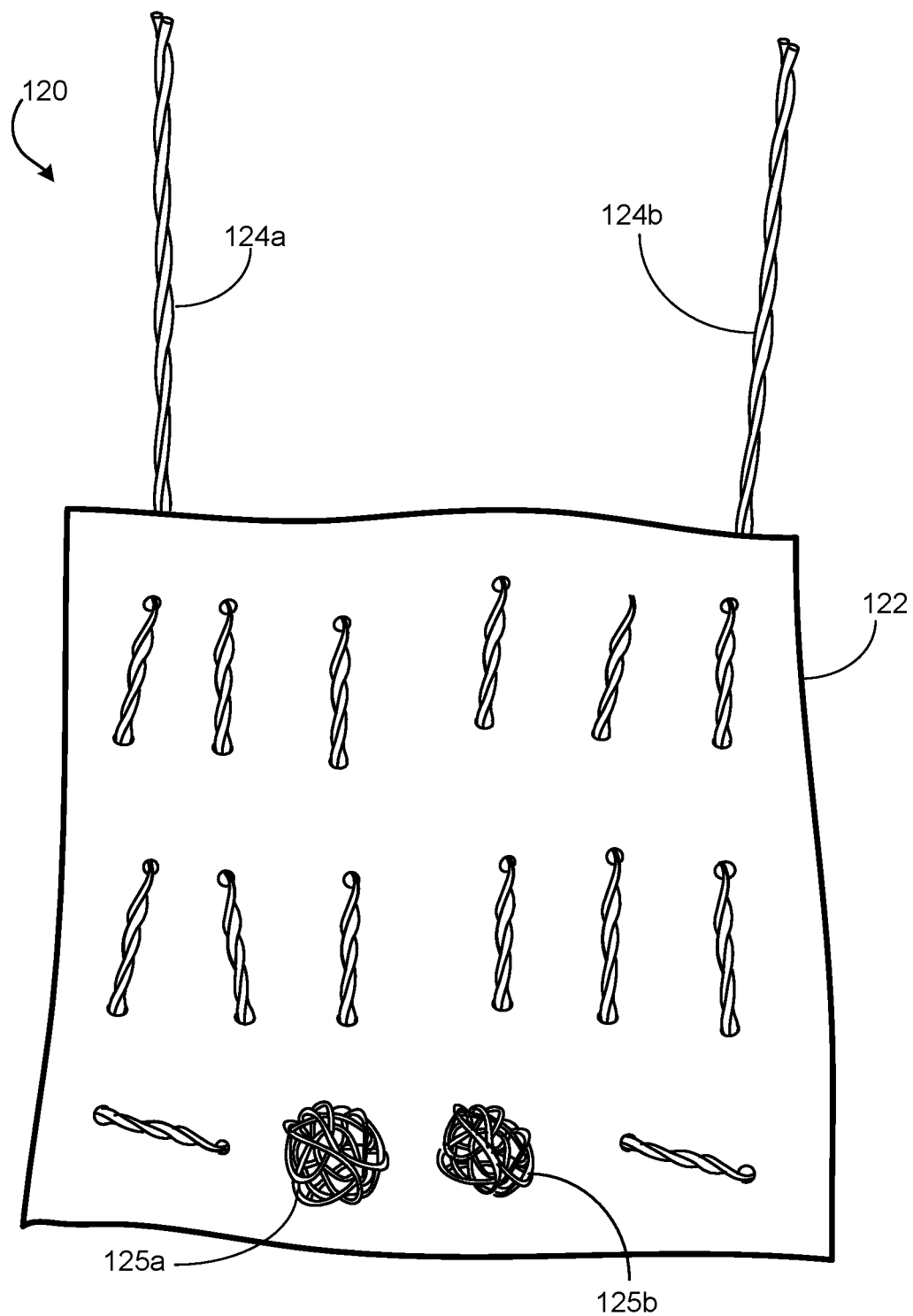
FIG. 1C depicts an image of an example flexible pressure sensor.

FIG. 1C depicts an image of an example flexible pressure sensor 120. As captured in FIG. 1C, the flexible pressure sensor 120 includes a pressure-sensitive sheet 122, e.g., a sheet of Velostat™, with a conductive thread, e.g., stainless steel wire, as a first electrode 124a and a second electrode 124b. Each of the first electrode 124a and second electrode 124b are sewn directly into the pressure-sensitive sheet 122, such that a portion of the electrode is in contact with a front surface of the pressure-sensitive sheet and a portion of the electrode is in contact with a back surface of the pressure-sensitive sheet. Other ways of routing the electrodes through holes in the pressure-sensitive sheet can also be used. As depicted, each electrode is threaded through the pressure-sensitive sheet 122 in multiple locations in a "switch-back" pattern, where each electrode has multiple lengths that are substantially parallel to each other. An end point of the first electrode 124a and an end point of the second electrode 124b are affixed to the pressure-sensitive sheet 122 by knots 125a and 125b, respectively. Of course, the end points can be affixed to the pressure-sensitive sheet using other attachment means, e.g., fasteners, adhesives, tape, etc.

Figure 2A:
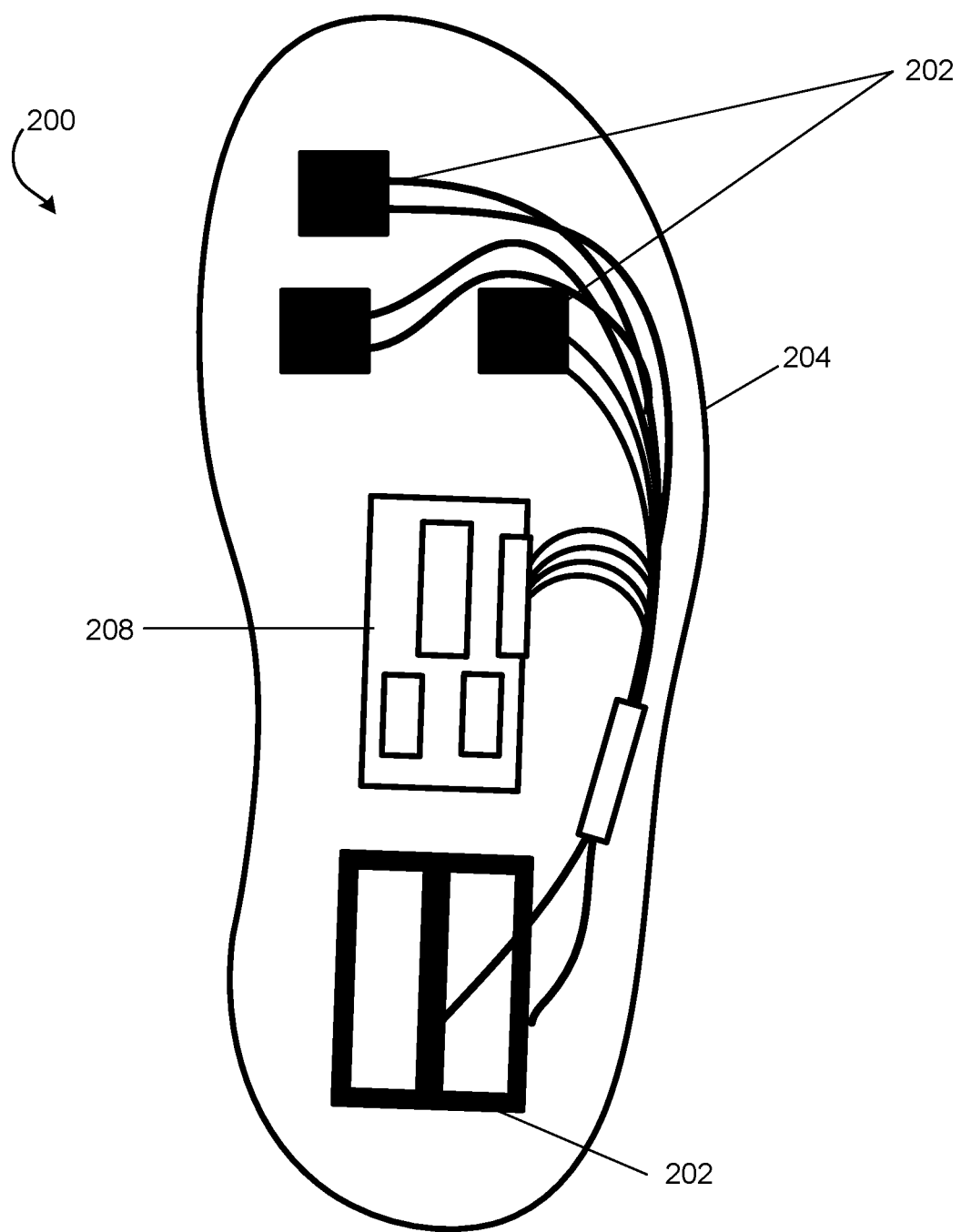
FIGS. 2A-2C depict views of an example system including flexible pressure sensors.

In some implementations, one or more flexible pressure sensors as described with reference to FIGS. 1A-1C are embedded in wearable devices, for example, in shoes, shirts/pants, safety gear (e.g., hard hat), gloves, virtual reality (VR)/augmented reality (AR) integration, sport training tools, grip strength tools, or the like. FIGS. 2A-2C depict views of an example system including flexible pressure sensors. FIG. 2A depicts a system 200 including multiple flexible pressure sensors 202 arranged, e.g., embedded, in a sole 204 of a shoe. As depicted, the multiple flexible pressure sensors 202 are distributed at different points of the sole, e.g., where the ball of a foot comes in contact with the sole 204, or where the heel of a foot comes in contact with the sole 204. Each of the multiple flexible pressure sensor 202 can be configured to measure an applied force, e.g., pressure, deformation, etc., to the flexible pressure sensor 202.

In some implementations, the multiple flexible pressure sensors 202 can each be integrated on a same pressure-sensitive sheet. In other words, a single sheet of pressure-sensitive material, e.g., Velostat™, can include multiple sets of first and second electrodes such that multiple flexible pressure sensors are formed adjacent to each other on the pressure-sensitive sheet. Each set of first and second electrodes can be utilized to measure applied force within the area defined by the electrodes on the pressure-sensitive sheet, e.g., between the parallel runs of the first and second electrodes.

The system 200 can additionally include a control unit 208, e.g., control unit 112, including a microcontroller, a wireless connectivity unit (e.g., Bluetooth and/or Wi-Fi enabled device), and a power source 210 (not shown) to provide power to the control unit 208, the flexible pressure sensors 202, etc. Control unit 208 can be configured to collect electrical measurements from the flexible pressure sensor, e.g., detect voltage differences between first and second electrodes. Control unit can additionally be configured to determine, from the collected electrical measurements, applied forces or ranges of applied forces indicated by the collected electrical measurements. In some implementations, as described with reference to FIG. 5 below, the control unit can be configured to generate force feedback responsive to determined applied forces.

Figure 2B:
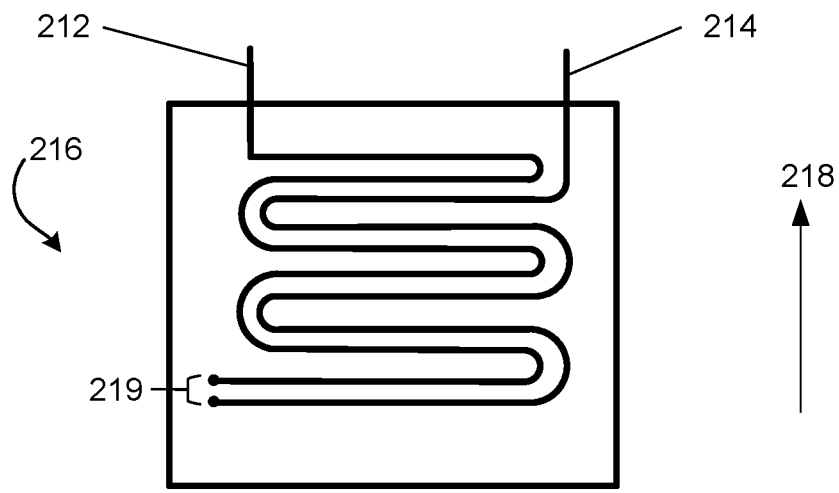
Figure 2C:
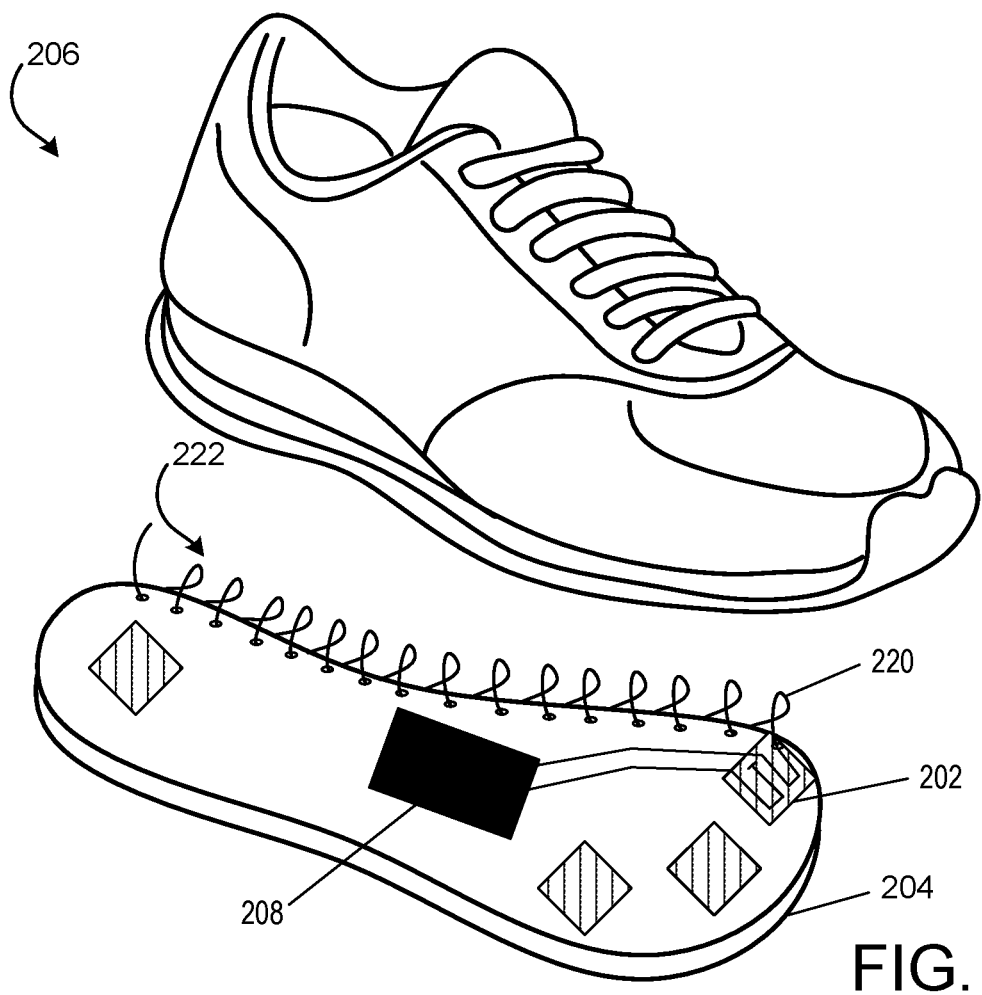

FIG. 2B depicts another example pattern of a first electrode 212 arranged with respect to a second electrode 214 for a flexible pressure sensor 216. As depicted in FIG. 2B, the first electrode 212 and second electrode 214 are arranged in a serpentine pattern, where a portion of the first electrode 212 and second electrode 214 that is arranged in the serpentine pattern is separated by a gap 219. By arranging the electrodes in the serpentine pattern, the flexible pressure sensor 216 may have improved accuracy and/or reliability when a force is applied normal (e.g., perpendicular to the pressure-sensitive material surface) to the surface of the flexible pressure sensor. The serpentine pattern may increase a portion of the sensor that includes parallel runs of the two electrodes over which there exists a gap between the two electrodes, and where the sensor can be activated along any point of the serpentine pattern by the application of a force. In other words, an applied force can be measured at different portions of the sensor that each include parallel runs of the two electrodes in the serpentine pattern, thereby increasing an area of the sensor over which an applied force can be measured by the sensor.

An amount of force required to active the flexible pressure sensor can depend in part on a distance between the parallel runs of the two electrodes, e.g., such that a larger gap requires a larger applied force and a smaller gap requires a smaller applied force. A selected gap between the first and second electrodes can be selected in part on a thickness of conductive thread utilized for the flexible pressure sensor and/or a thickness of the pressure-sensitive layer. In one example, a gap of 1-10 mm can be selected for the flexible pressure sensor.

In some implementations, a flexible pressure sensor may be utilized to measure force applied parallel, e.g., along direction 218 to the pressure-sensitive sheet, e.g., when an electrode is pulled such that the pressure-sensitive sheet is deformed and a change in resistance measured.

In some implementations, one or more flexible pressure sensors can be embedded at a seam 222 of a shoe 206. The seams of the shoe can be stitched together with conductive thread forming an electrode 220 of a flexible pressure sensor 202 such that stresses of the manufacturing process (e.g., a pulled/stressed seam) and/or stresses generated during wear of the shoe can be identified using measurements collected from the flexible pressure sensors.

Figure 3:
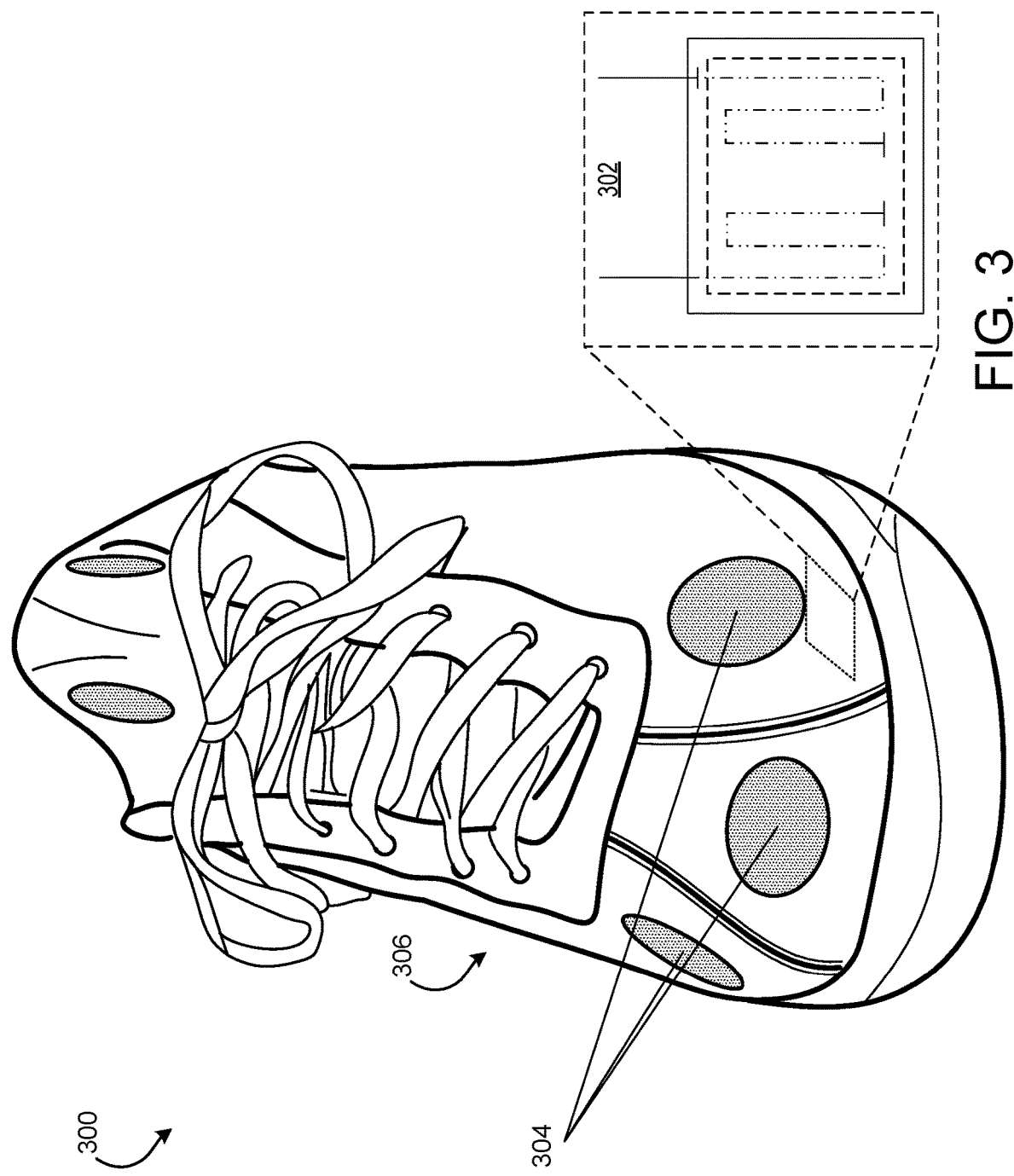
FIG. 3 depicts a schematic of another example system including flexible pressure sensors.

In some implementations, a system including the flexible pressure sensors can include light sources, for example, light-emitting diodes (LEDs) embedded into a wearable device. A wearable device including the flexible pressure sensors and light sources can be, for example, a shoe, a glove, a safety garment (e.g., hard hat), or the like. FIG. 3 depicts an image of an example system 300 including flexible pressure sensors 302 and embedded light sources 304 in a shoe 306. The light sources 304, e.g., LEDs, can be embedded into the shoe 306 such that a user wearing the shoe 306 can observe light emitted from the LEDs, for example, by embedding the light sources on an external surface of the shoe and/or embedded within/underneath a mesh layer of the shoe 306.

Light sources 304 can provide a visual feedback responsive to measurements made by the flexible pressure sensors 302. Visual feedback can include, for example, providing a light signal from one or more light sources 304 responsive to measuring an applied force by a flexible pressure sensor 302, e.g., turning on/off the light source, changing an intensity of the light source, changing a color emitted by the light source. The visual feedback can provide, for example, stride adjustment information to a user wearing the shoe. The light sources 304 can receive control signals from a control unit (not shown) (e.g., microcontroller) in data communication with the light sources 304 and the flexible pressure sensors 302. System 300 can additionally include a power source (not shown), e.g., a lithium ion battery, configured to provide power to the control unit, flexible pressure sensors 302, and light sources 304.

In some implementations, a light source 304 can be embedded within the shoe 306 at a location corresponding (e.g., at or near) to a location of a flexible pressure sensor 302 such that when a force is measured at the flexible pressure sensor 302, the corresponding light source 304 can emit a light signal. For example, when a person wearing the shoe applies a force to the toe of the shoe including a flexible pressure sensor 302, an LED located at the toe of the shoe can light up.

Figure 4:
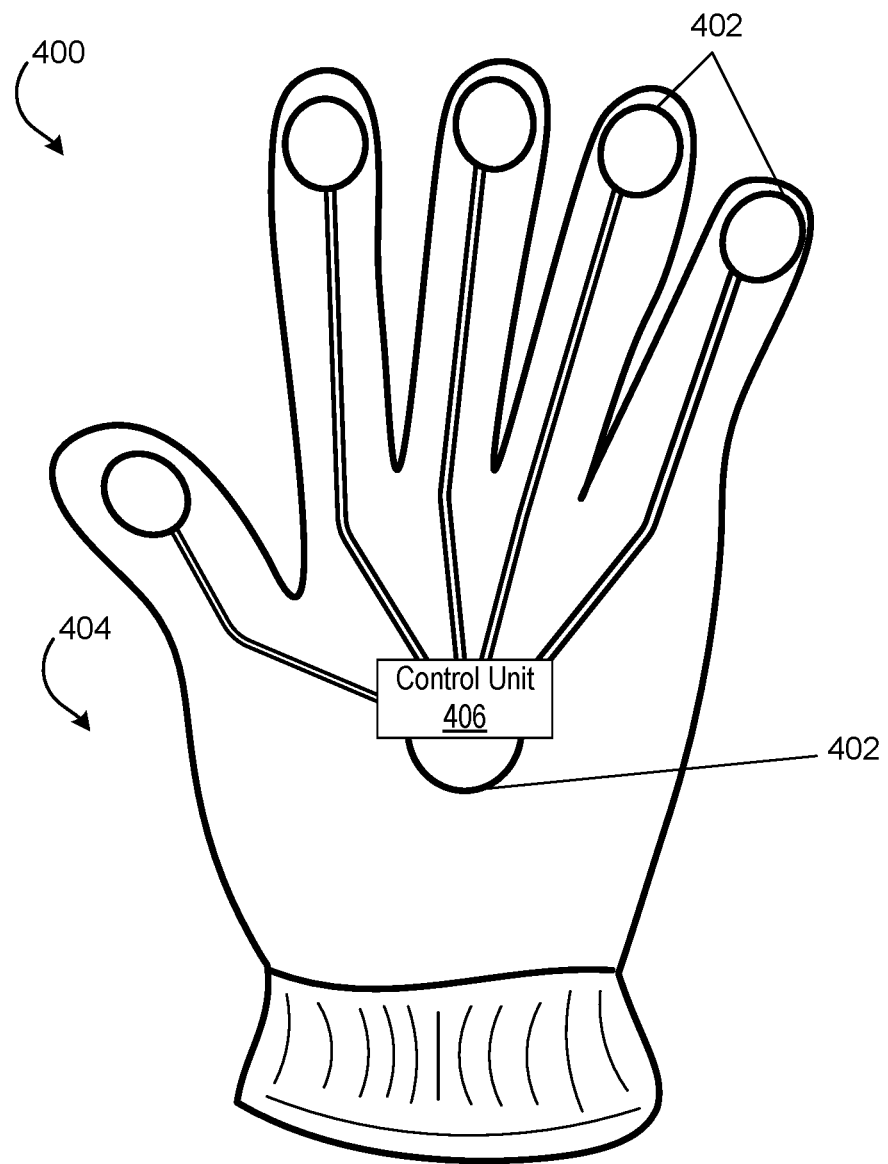
FIG. 4 depicts a schematic of another example system including flexible pressure sensors.

In some implementations, a system 400 including flexible pressure sensors 402 can be a wearable glove 404. FIG. 4 depicts another example system including flexible pressure sensors. Glove 404 can be a wearable device for VR/AR integration, e.g., to measure gestures or touch actions performed by a user wearing the glove 404. Glove 404 can include flexible pressure sensors at the fingertips of the glove, on a palm of the glove, and/or on a back of the hand surface of the glove. System 400 can additionally include a control unit 406 in data communication with the flexible pressure sensors, e.g., a microcontroller, and a power source 408 for operating the system 400.

In some implementations, data captured by the flexible pressure sensors 402 can be provided, e.g., over a wireless network 118, to a user device 116. In one example, data captured by the system 400 can be utilized by a VR/AR application to control operations within the application. For example, data captured by the flexible pressure sensors 402 can provide fine motor control by indicating bend/flex when picking up small objects. In another example, data captured by the flexible pressure sensors 402 can provide force or pressure indication when pushing/manipulating an object, which can be used to mirror forces required to move objects of different weights.

As described above with reference for FIG. 1A, the flexible pressure sensor 100 is electrically connected to a control unit 112, which can include a microcontroller configured to collect measurement data from the flexible pressure sensor in response to applied forces. The control unit 112 can provide the measurement data to a user device via a wireless or wired connection to the network. Analysis of the measurement data generated by the flexible pressure sensor can be performed by the control unit 112, by the user device 116, or a combination thereof.

Figure 5:
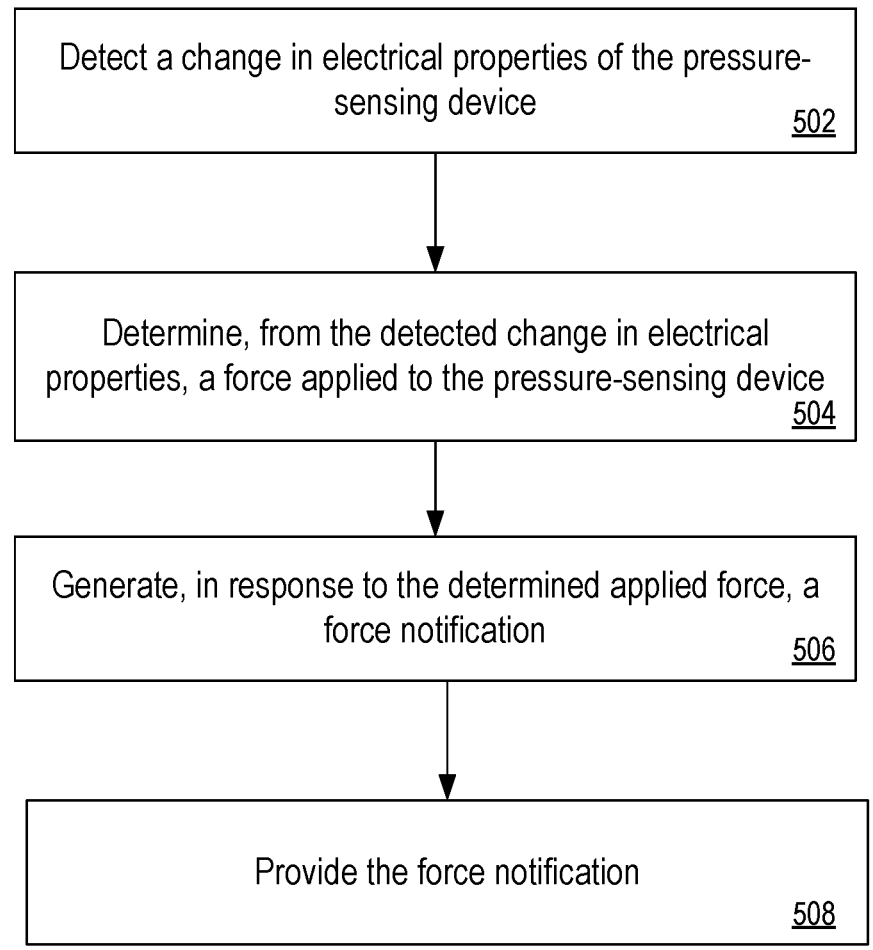
FIG. 5 is a flow diagram of an example process of a flexible pressure sensor.

FIG. 5 is a flow diagram of an example process of a flexible pressure sensor. Though described with reference to FIG. 5 as processes performed by the control unit, e.g., control unit 112 including a microcontroller, one or more of the processes described can be performed by a user device, cloud-based server, or a combination thereof in data communication with the control unit 112. A control unit detects a change in electrical properties of a pressure-sensing device (502). In one example, the control unit can monitor a voltage across the first electrode and second electrode of a pressure-sensitive region using a voltage sensor. The control unit can also compare a detected change in voltage to previous voltage changes and/or to a threshold voltage change. Detecting a change in voltage can include detecting a change in voltage that is greater than, or less than, a particular threshold.

In some implementations, a baseline measurement, e.g., a voltage across the first electrode and second electrode, can be measured for the flexible pressure sensor. The baseline measurement can be collected during a manufacturing/installation process and can be utilized by the control unit as a reference value for the flexible pressure sensor as under nominally free of external applied force. The baseline electrical measurement can be utilized as a calibration point to perform differential measurements between a no-force scenario and an applied-force scenario. The detected change in electrical properties can be a change in the voltage drop measured across the first electrode (e.g., a positive electrode) and the second electrode (e.g., ground or negative electrode).

In some implementations, the pressure sensing-device includes multiple pressure-sensitive input regions such that the control unit can detect multiple changes in electrical properties of two or more pressure-sensitive input regions. The control unit can detect a respective change for each of the multiple pressure-sensitive input regions, where the changes in electrical properties of each of the multiple pressure-sensitive input regions can be indicative of a respective, different applied force applied to the multiple pressure-sensitive input regions. For example, a respective pressure-sensitive input region located at each fingertip region of a glove, e.g., glove 404, can read a respective change in electrical properties (e.g., a respective voltage difference) corresponding to a different applied force by a user to each fingertip of the glove.

The control unit determines an applied force to the pressure-sensing device based on the detected change to the electrical properties (504). The control unit can determine, from the detected change in the electrical properties of the one or more pressure-sensitive input regions, an applied force that corresponds to the detected change, e.g., corresponding to a detected voltage drop. In this example, the control unit can include, for a range of applied forces, data indicating voltage changes or ranges of voltage changes corresponding to the range of applied forces. For example, the control unit can determine, from the detected change in voltage between a first electrode and second electrode, an applied force or range of applied forces at a pressure-sensing device located at a heel region of a sole of a shoe, e.g., sole 204 of shoe 206.

In some implementations, the control unit can include data indicating voltage changes or ranges of voltage changes corresponding to different types of applied forces, e.g., pressure applied perpendicular to a surface of the pressure-sensitive region, deformation of the pressure-sensitive region (e.g., folding of the pressure-sensitive sheet 122), pulling of one or more of the electrodes of the pressure-sensitive region, etc.

The control unit generates a force notification in response to the determined applied force (506). A force notification can include an audio/visual notification, e.g., light signal emitted from a light source embedded in a system including the flexible pressure sensor, audible feedback via a speaker. The control unit can generate a particular force notification based on the determined applied force and/or a location of the determined applied force, e.g., the determined applied force exceeds a threshold force, the determined applied force is localized to a particular pressure-sensitive region of multiple pressure-sensitive regions of the flexible pressure sensor, etc. For example, the control unit can generate a force notification including emitting light from an LED embedded in a shoe in response to a threshold applied force determined to be applied to a particular pressure-sensitive region of the flexible pressure sensor. In another example, the control unit can provide a first light signal (e.g., blue light) in response to a first range of applied forces and a second light signal (e.g., red light) in response to a second range of applied forces.

In some implementations, the control unit can generate a first force notification when a first pressure-sensitive region is determined to have at least a threshold applied force and second, different force notification when a second pressure-sensitive region is determined to have at least a threshold applied force. For example, a first force notification can be emitting a light signal from an LED located at a first fingertip of a glove in response to a threshold applied force at a pressure-sensitive region located at the first fingertip and a second force notification can be emitting a light signal from an LED located at a second fingertip of the glove in response to a threshold applied force at a pressure-sensitive region located at the second fingertip.

In some implementations, the control unit generates a force notification including information of the determined force. The force notification can include displayed information in an application environment of an application on a user device. For example, the force notification can include information related to one or more determined applied forces and locations of the determined applied forces with respect to the pressure-sensitive regions of a flexible pressure sensor. The information related to the one or more determined applied forces can also include, for example, timing related to the applied forces, sequences of applied forces detected at multiple different pressure-sensitive regions, etc. In one example, a sequence of applied forces detected at multiple different pressure-sensitive regions located on a sole 204 of a shoe 206 can be utilized to provide stride adjustment feedback.

The control unit provides force notification (508). The control unit can provide the visual notification, e.g., emitted light signal from a light source, and/or information presented in an application environment of an application on user device. For example, the control unit can generate or update a user interface to present pressure measurements for each pressure-sensitive region, e.g., in a time series list or graph of changes in pressure readings over time such as during a training exercise.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor will receive instructions and data from a read only memory or a random access memory or both. Elements of a computer can include a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical user interface or a Web browser through which a user may interact with an implementation, or any appropriate combination of one or more such back end, middleware, or front end components. The components of the system may be interconnected by any appropriate form or medium of digital data communication (e.g., a communication network). Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

Figure 6:
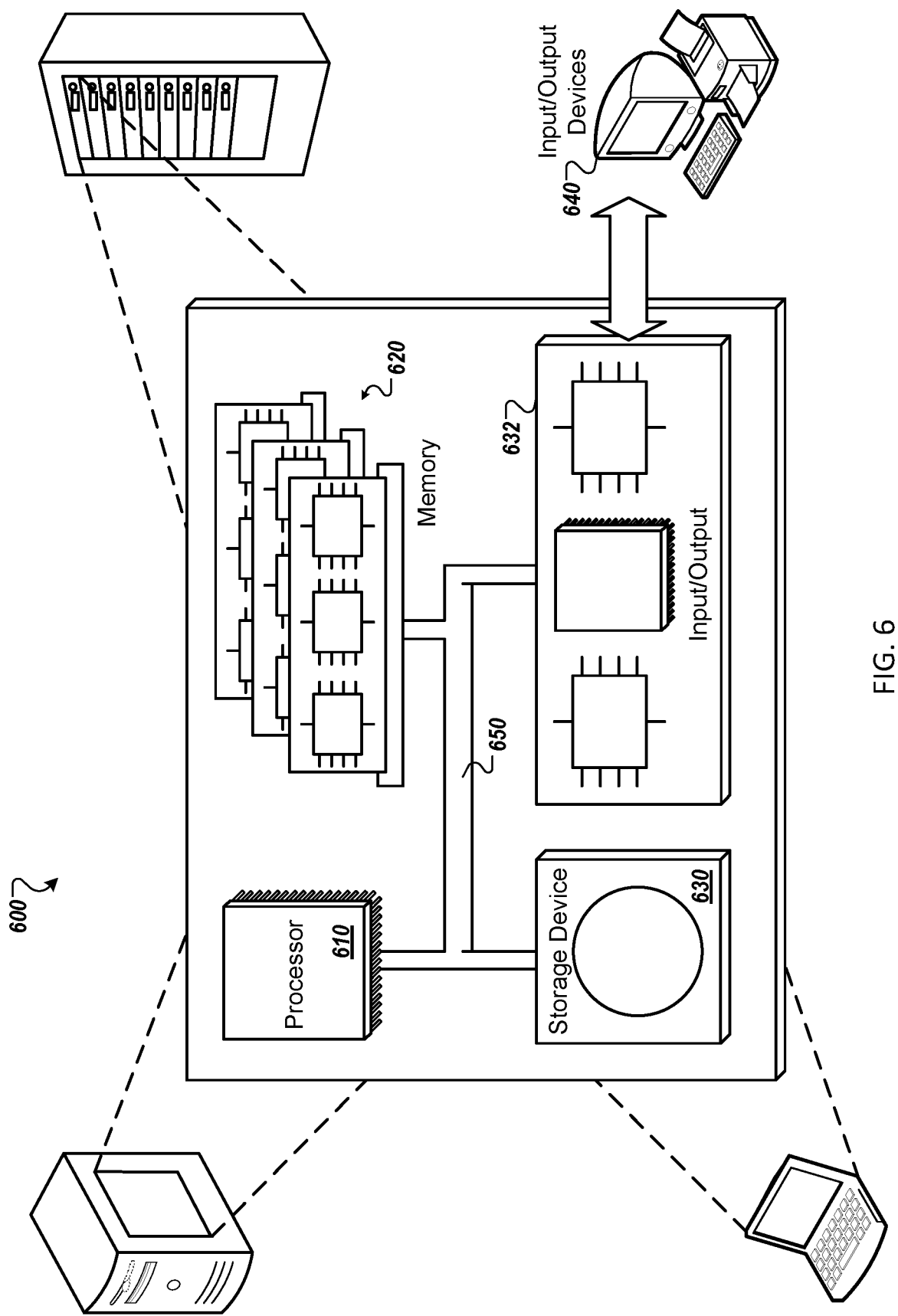
FIG. 6 depicts a schematic of an example computer system.

An example of one such type of computer is shown in FIG. 6, which shows a schematic diagram of a generic computer system 600. The system 600 can be used for the operations described in association with any of the computer-implemented methods described previously, according to one implementation. The system 600 includes a processor 610, a memory 620, a storage device 630, and an input/output device 640. Each of the components 610, 620, 630, and 640 are interconnected using a system bus 650. The processor 610 is capable of processing instructions for execution within the system 600. In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the system 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the system 600. In one implementation, the storage device 630 is a computer-readable medium. In various different implementations, the storage device 630 may be a floppy disk device, a hard disk device, an optical disk device, or a tape device.

The input/output module 632 includes hardware or hardware and software for interfacing system 600 with the input/output device 640 or other devices or interfaces.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:

1. A pressure-sensing device comprising:
a pressure-sensitive sheet;
one or more pressure-sensitive input regions disposed along the pressure-sensitive sheet, each pressure-sensitive input region comprising,
a first conductive thread comprising a first length sewn into the pressure-sensitive sheet such that some segments of the first length of the first conductive thread are disposed on one surface of the pressure-sensitive sheet, additional segments of the first length pass through the pressure-sensitive sheet, and other segments of the first length are disposed on another surface that is opposite to the one surface of the pressure-sensitive sheet; and
a second conductive thread comprising a second length sewn into the pressure-sensitive sheet such that some segments of the second length of the second conductive thread are disposed on the one surface of the pressure-sensitive sheet, additional segments of the secondment length pass through the pressure-sensitive sheet, and other segments of the second length are disposed on the another surface that is opposite to the one surface of the pressure-sensitive sheet.

2. The device of claim 1, wherein the first conductive thread comprises a first lead electrically connected to a positive electrode of the pressure-sensing device and the second conductive thread comprises a second lead electrically connected to a negative electrode of the pressure-sensing device.

3. The device of claim 1, wherein the pressure-sensitive sheet comprises an electrically conductive material, and
wherein an electrical conductance of the pressure-sensitive sheet depends in part on an externally applied force to i) the pressure-sensitive sheet, ii) the first conductive thread, iii) the second conductive thread, or iv) a combination thereof.

4. The device of claim 3, wherein the pressure-sensitive sheet comprises Velostat™.

5. The device of claim 1,
wherein the first length of the first conductive thread passes through the pressure-sensitive sheet through a plurality of holes in the pressure-sensitive sheet, and
wherein the second length of the second conductive thread passes through the pressure-sensitive sheet through a plurality of holes.

6. The device of claim 5, wherein the first length of the first conductive thread that is sewn into both sides of the pressure-sensitive sheet is substantially parallel to the second length of the second conductive thread that is sewn into both sides of the pressure-sensitive sheet.

7. The device of claim 6, wherein the first length of the first conductive thread and the second length of the second conductive form a serpentine pattern.

8. A system, comprising:
a pressure-sensing device comprising:
a pressure-sensitive sheet; and
one or more pressure-sensitive input regions disposed along the pressure-sensitive sheet, each pressure-sensitive input region comprising,
a first conductive thread comprising a first length sewn into the pressure-sensitive sheet such that some segments of the first length of the first conductive thread are disposed on one surface of the pressure-sensitive sheet, additional segments of the first length pass through the pressure-sensitive sheet, and other segments of the first length are disposed on another surface that is opposite to the one surface of the pressure-sensitive sheet; and
a second conductive thread comprising a second length sewn into the pressure-sensitive sheet such that some segments of the second length of the second conductive thread are disposed on the one surface of the pressure-sensitive sheet, additional segments of the secondment length pass through the pressure-sensitive sheet, and other segments of the second length are disposed on the another surface that is opposite to the one surface of the pressure-sensitive sheet
one or more processors; and
a computer-readable storage device coupled to the one or more processors and having instructions stored thereon which, when executed by the one or more processors, cause the one or more processors to perform operations comprising:
detecting, from the pressure-sensing device, a change in electrical properties of the pressure-sensing device; and
determining, from the detected change in electrical properties, a force applied to the pressure-sensing device.

9. The system of claim 8, further comprising:
a light source in data communication with the one or more processors; and
a power source configured to provide power to the light source,
wherein the light source is configured to emit light signal in response to the detected change in electrical properties.

10. The system of claim 9, further comprising a shoe, wherein the pressure-sensing device is retained within a portion of the shoe.

11. The system of claim 10, further comprising:
generating, in response to the determined force applied to the pressure-sensing device, a stride adjustment recommendation; and
providing, the stride adjustment recommendation.

12. The system of claim 11, wherein the light source is retained within a portion of the shoe, and
wherein providing the stride adjustment recommendation comprises emitting the light signal from the light source.

13. The system of claim 11, wherein providing the stride adjustment recommendation comprises providing a notification in a user interface on a user device.

14. The system of claim 10, wherein at least a portion of the pressure sensing device is located between two seams of the shoe.

15. The system of claim 8, further comprising a pressure-sensitive glove, wherein the pressure-sensing device is retained within a fingertip or palm of the pressure-sensitive glove.

16. The system of claim 8, further comprising:
generating, in response to the determined force applied to the pressure-sensing device, a force notification; and
providing, the force notification.

* * * * *